United States Patent [19]

Burk

[11] Patent Number: 4,944,594
[45] Date of Patent: Jul. 31, 1990

[54] APPARATUS AND METHOD FOR MEASURING DARK AND BRIGHT REFLECTANCES OF SHEET MATERIAL

[75] Inventor: Gary N. Burk, Columbus, Ohio

[73] Assignee: Process Automation Business, Inc., Columbus, Ohio

[21] Appl. No.: 187,204

[22] Filed: Apr. 28, 1988

[51] Int. Cl.$^5$ .............................................. G01J 3/42
[52] U.S. Cl. .................................. 356/446; 356/429; 356/434; 356/73
[58] Field of Search ............... 356/429, 432, 433, 434, 356/445, 446, 73; 350/330, 331, 338

[56] References Cited

U.S. PATENT DOCUMENTS

| | | | |
|---|---|---|---|
| 1,950,975 | 3/1934 | Davis | 356/434 |
| 3,455,637 | 7/1969 | Howard . | |
| 3,936,189 | 2/1976 | DeRemigis | 356/429 |
| 4,076,421 | 2/1978 | Kishner | 356/446 |
| 4,224,513 | 9/1980 | Casey . | |
| 4,589,735 | 8/1986 | Saunders | 350/338 |
| 4,624,572 | 11/1986 | van den Bosch | 356/446 |
| 4,678,325 | 7/1987 | Lehtikoski et al. . | |
| 4,715,715 | 12/1987 | Howarth et al. . | |

Primary Examiner—Vincent P. McGraw
Assistant Examiner—S. A. Turner
Attorney, Agent, or Firm—Killworth, Gottman, Hagan & Schaeff

[57] ABSTRACT

Apparatus (10) and methods for measuring dark and bright reflectances of translucent sheet material (2) are disclosed. The apparatus (10) comprises first optical means for illuminating one side of the sheet material (2) with a source of electromagnetic radiation. A portion of the radiation is transmitted through the sheet material (2) and another portion of the radiation is reflected by the sheet material. The apparatus (10) also comprises optical gating means (30) that is positioned adjacent the other side of the sheet material (2) in a fixed position relative to the first optical means. The optical gating means (30) absorbs substantially all of the transmitted portion of the radiation when switched to a dark state and reflects substantially all of the transmitted portion of the radiation back through the sheet material (2) when switched to a bright state. The apparatus (10) further comprises second optical means for collecting the reflected portion of the radiation and the portion of the transmitted portion of the radiation reflected by the optical gating means (30) and retransmitted through the sheet material (2) to provide a total reflectance. The total reflectance has a dark reflectance intensity when the optical gating means (30) is in the dark state and a bright reflectance intensity when the optical gating means is in the bright state. The apparatus also comprises sensing means (60), responsive to radiation collected by the second optical means, for providing a dark signal having a magnitude corresponding to the dark reflectance intensity and a bright signal having a magnitude corresponding the bright reflectance intensity. The dark and bright signals can be incorporated in known formulae to compute values for quality attributes of the sheet material (2) including opacity and color.

18 Claims, 2 Drawing Sheets

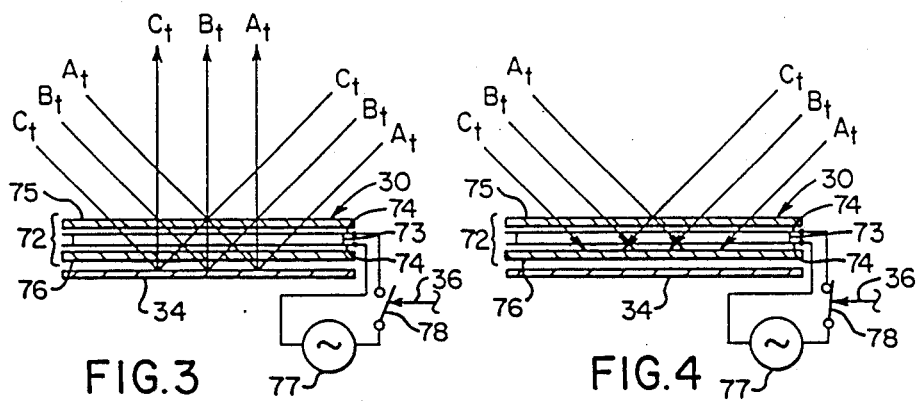
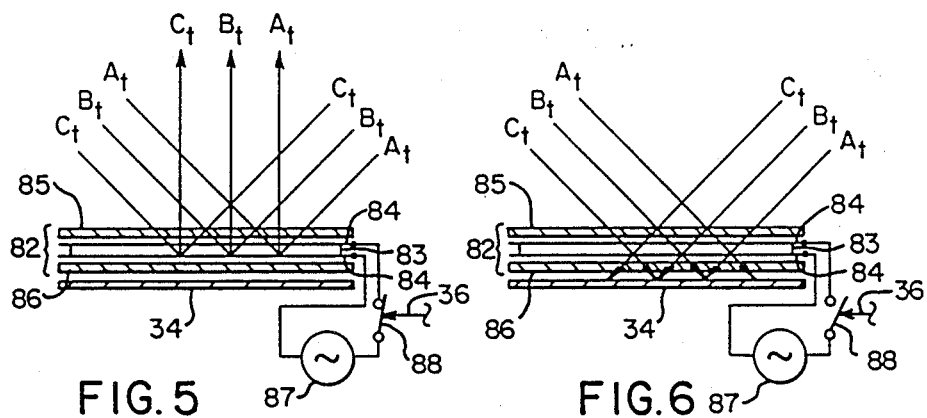

APPARATUS AND METHOD FOR MEASURING DARK AND BRIGHT REFLECTANCES OF SHEET MATERIAL

BACKGROUND OF THE INVENTION

1. Technical Field

The present invention relates generally to process automation for systems which manufacture sheet materials, and more particularly to apparatus and methods for on-line measurement of various quality attributes of such materials, wherein measurement is based on reflectance. Specifically, this invention pertains to apparatus and methods for use in providing measurements of quality attributes wherein the measurements require that two separate determinations of reflectance be made as the sheet material is alternately positioned against dark and light backgrounds.

2. Related Art

It is desirable to know the reflectance of continuously-produced sheet materials for several reasons. In the paper industry for example, the reflectance may be indicative of a variety of quality attributes including gloss, smoothness, opacity, and color to mention a few.

For some quality attributes such as opacity and color, it is desirable to know two reflectance values for the sheet material, one being obtained when the sheet is positioned against a dark background, and the other being obtained when the sheet is positioned against a light background.

The color of the material can be ascertained by illuminating the material with white light and measuring the reflectance therefrom for each of a plurality of wavelength bands in the visible region of the electromagnetic spectrum. Such measurements can be accomplished by using a spectrophotometer such as that disclosed in U.S. Pat. No. 4,076,421 Kishner, for example. However, in the manufacture of paper products, the manufacturer is concerned with the color of the material as it appears to a consumer who observes the material in the form of a wound-up roll or a stack of individual layers as in a book or a napkin. To determine the color (as seen by an observer) of a roll of translucent sheet material such as a thin paper product, it would be necessary to measure the reflectance from a stack of individual plys of the material. This presents a problem in on-line color measurement because typically only a single ply is involved and the observer would perceive a different color if only a single ply of the material were observed. The difference in perception is due to the fact that the opacity of a single ply of translucent material is different from the opacity of multiple plys. Thus, in order to make a color measurement that is meaningful to the manufacturer, it is necessary to account for the opacity of the material. This may be accomplished by providing the forementioned plurality of reflectance measurements twice, once with a dark background positioned against the material to obtain the "dark reflectance", and once with a lighter background positioned against the material to obtain the "bright reflectance", and using known formulae to calculate the opacity-compensated color. Normally, a spectrophotometer or other instrument remains in one location on one side of the moving sheet material while a mechanical device shuttles the dark and light backgrounds successively into the radiation path and against the other side of the sheet so that sequential measurements are made. This arrangement is undesirable for a number of reasons including differential dust buildup on the dark and light backgrounds, and the need to manufacture and maintain cumbersome mechanical devices.

A recent attempt to circumvent this arrangement uses the idea that since multiple plys of the material best represent the desired background, that is precisely what should be provided (See U.S. Pat. No. 4,715,715.). However, while this idea is admirable in its simplicity, it appears not to account for the fact that color changes occur within a single run of material. Moreover, it appears to require a change in background between successive runs, thus adding to the papermaker's duties.

Accordingly, there is a need for a device for measuring dark and bright reflectances while providing alternating backgrounds in a fixed position with respect to the source of illumination and, more specifically, for such a device that obviates mechanical parts while providing uniform standards for the alternating backgrounds.

SUMMARY OF THE INVENTION

The present invention provides apparatus and methods for measuring dark and bright reflectances for translucent sheet material in accordance with the above-stated need.

The apparatus comprises first optical means for illuminating one side of the sheet material with a source of optical electromagnetic radiation of substantially uniform intensity so that a portion of the radiation is transmitted through the sheet material and another portion of the radiation is reflected by the sheet material. The apparatus also comprises optical gating means positioned adjacent the other side of the sheet material in fixed position relative to the source. The optical gating means absorbs substantially all of the transmitted portion of the radiation when switched to a dark state and reflects substantially all of the transmitted portion of the radiation back into the sheet material when switched to a bright state. The apparatus further comprises second optical means for collecting the reflected portion of the radiation and the portion of the transmitted portion of the radiation reflected by the optical gate means and retransmitted through the sheet material to provide a total reflectance. The total reflectance has a dark reflectance intensity when the optical gate means is in the dark state and a bright reflectance intensity when the optical gate means is in the bright state. The apparatus also comprises sensing means, responsive to the radiation collected by the second optical means, for providing a dark signal having a magnitude corresponding to the dark reflectance intensity and a bright signal having a magnitude corresponding to the bright reflectance intensity. The dark and bright signals can be used to compute the reflective opacity of the sheet material.

The apparatus can also be used so that the first optical means directly illuminates the optical gating means when switched to the bright state so that a portion of the radiation is reflected by the optical gating means. The second optical means collects the portion reflected by optical gating means to provide a reference reflectance and the sensing means provides a reference signal having a magnitude corresponding to the intensity of the reference reflectance. As a result, a standardized reflective opacity of the sheet material can be computed from the bright and dark signals and the reference signal.

The optical gating means comprises a liquid crystal device and a backing plate. The liquid crystal is positioned between the sheet material and the backing plate and has an input for connecting and disconnecting a voltage source to switch the liquid crystal between the dark and bright states. In a first embodiment, the liquid crystal is a field-effect liquid crystal and the backing plate has a reflective surface facing the liquid crystal. As a result, the liquid crystal absorbs the transmitted portion of the source in the dark state when the voltage source is connected to the input thereof and the backing plate reflects the transmitted portion of the source in the bright state when the voltage source is disconnected from the input thereof making the liquid crystal transparent. In a second embodiment, the liquid crystal is a dynamic-scattering liquid crystal and the backing plate has an absorptive surface facing the liquid crystal. As a result, the liquid crystal reflects the transmitted portion of the radiation in the bright state when the voltage source is connected to the input thereof and the backing plate absorbs the transmitted portion of the radiation in the dark state when the voltage source is disconnected from the input thereof making the liquid crystal transparent.

The present invention also meets the stated need by providing a method for measuring the dark and bright reflectances of translucent sheet material. The method comprises the steps of illuminating one side of the sheet material with a source of optical electromagnetic radiation of substantially uniform intensity. A portion of the radiation is transmitted through the sheet material and another portion of the radiation is reflected by the sheet material. The method also comprises the step of positioning an optical gate adjacent the other side of the sheet material in a fixed position relative to the source. The optical gate absorbs substantially all of the transmitted portion of the radiation when the optical gate is switched to a dark state and reflects substantially all of the transmitted portion of the radiation back through the sheet material when the optical gate is switched to a bright state.

The method further comprises the step of collecting the reflected portion of the radiation and the portion of the transmitted portion of the radiation reflected by the optical gate and retransmitted through the sheet to provide a total reflectance. The total reflectance has a dark reflectance intensity when the optical gate is in the dark state and a bright reflectance intensity when the optical gate is in the bright state. The method also comprises the step of providing a dark signal having a magnitude corresponding to the dark reflectance intensity and a bright signal having a magnitude corresponding to the bright reflectance intensity. Accordingly, it is an object of the present invention to provide apparatus and methods for measuring the dark and bright reflectances of translucent sheet material, and to provide such apparatus and methods which employ optical gate means having alternating backgrounds in a fixed position with respect to the first optical means to obviate the requirement for moving mechanical parts while providing uniform reflectance standards. Other objects and advantages of the invention will be apparent from the following description, the accompanying drawings, and the appended claims.

BRIEF DESCRIPTION OF THE DRAWINGS

FIGS. 3 and 4 are schematic drawings of a first embodiment of the liquid crystal, a field-effect type, in the bright and dark states, respectively, in accordance with the present invention.

FIGS. 5 and 6 are schematic drawings off a second embodiment of the liquid crystal, a dynamic-scattering type, in the bright and dark states, respectively, in accordance with the present invention.

DESCRIPTION OF PREFERRED EMBODIMENTs

Figure 1:
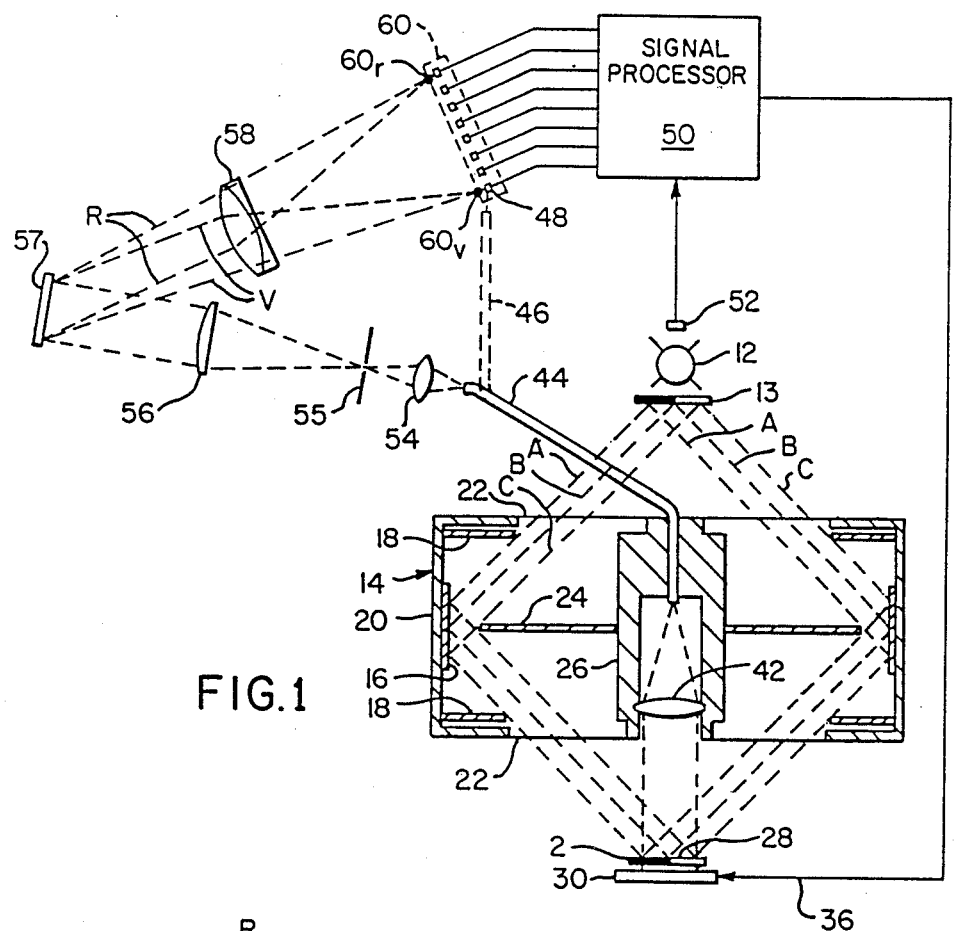
FIG. 1 is a schematic drawing of an embodiment of the invention, illustrating a spectrophotometer and a liquid crystal positioned behind the sheet material.

An apparatus for measuring dark and bright reflectances of translucent sheet material 2 is indicated generally at 10 in FIG. 1 and comprises first optical means, optical gating means, second optical means and sensing means. The first optical means comprises a source 12 which provides optical electromagnetic radiation of substantially uniform intensity through a diffusing screen 13 and an optical system 14 which includes a cylindrical reflector 16 and a pair of annular baffles 18 supported on a cylindrical frame 20 between two glass annuli 22 and an annular baffle 24 supported on a central housing 26. Central housing 26 is axially supported within cylindrical frame 20 between glass annuli 22. In a first embodiment of the present invention source 12 provides a source of monochromatic radiation or light to measure the opacity at one wavelength. Rays of illumination emanating from screen 13, such as rays A, B, and C, enter optical system 14, which is circularly symmetrical, and follow a path defined by annular baffles 18 and 24 and reflector 16. Reflector 16, which is preferably a mirror, directs the rays inward toward sheet material 2 at angles of approximately 45 degrees from the normal of sheet material 2. The rays from reflector 16 converge toward sheet material 2 and form a circular spot 28 of illumination of uniform intensity on sheet material 2. The uniformity of spot 28 is controlled by the degree to which screen 13 diffuses the light.

Figure 2:
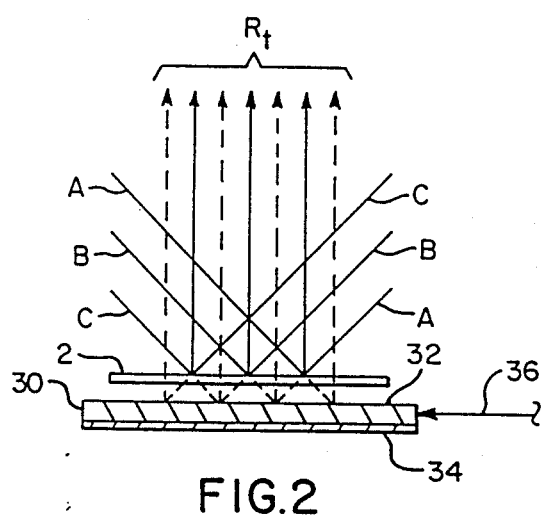
FIG. 2 is an enlarged view of the liquid crystal and the sheet material of FIG. 1.

Referring in more detail to FIG. 2, a portion of the light rays is transmitted through sheet material 2 and another portion of the light rays is reflected by sheet material 2. The portion of light transmitted through sheet material 2 impinges upon optical gating means 30, which is positioned adjacent the other side of sheet material 2 in a fixed position relative to the first optical means or optical system 14. Optical gating means 30 comprises a liquid crystal 32 and a backing plate 34. Liquid crystal 32 is positioned between sheet material 2 and backing plate 34 and has an input 36 for connecting and disconnecting a voltage source (not shown) to switch liquid crystal 32 between a dark state and a bright state. Optical gate means 30 absorbs substantially all of the transmitted portion of the light when switched to the dark state and reflects substantially all of the transmitted portion of the light back through sheet material 2 when switched to the bright state. This will be discussed below in more detail.

Apparatus 10 also comprises second optical means for collecting the portion of light reflected by sheet material 2, and the portion of the light transmitted through sheet material 2 that is reflected by optical gate means 30 and retransmitted through the sheet material, to provide a total reflectance R(t). The total reflectance has a dark reflectance intensity R(d) when optical gate means 30 is in the dark state and a bright reflectance intensity R(b) when optical gate means 30 is in the bright state. The second optical means comprises a lens 42 and a fiber optics bundle 44, both of which are mounted in central housing 26. Lens 42 collects the light (R(t)) and focuses it onto fiber optics bundle 44 which transmits the light as indicated by dashed line 46 to a photodetector 48.

In this monochromatic embodiment of the present invention, the single photodetector 48 constitutes the sensing means. The sensing means is responsive to the second optical means and provides a dark signal having a magnitude corresponding to the dark reflectance intensity and a bright signal having a magnitude corresponding to the bright reflectance intensity. The dark and bright signals produced by photodetector 48 are provided to a signal processor 50 which processes the signals in a manner that depends upon the specific application. For example, signal processor 50 might be used to amplify the signals or to convert the signals to digital signals for subsequent processing. The signal processor, however, forms no part of the present invention. A reference photodetector 52 is located adjacent source 12 in order to monitor the intensity of the radiation. The signal produced by photodetector 52 is also provided to signal processor 50 to properly bias the dark and bright signals provided by photodetector 48.

In a second embodiment of the present invention, source 12 provides visible white light and is preferably a pulsed xenon flashtube. The xenon flashtube can provide a short, intense pulse of broad spectrum illumination. Furthermore, the second optical means separates the total reflectance R(t) into its component wavelengths, so that there is a dark reflectance intensity R(d) and a bright reflectance intensity R(b) for each component wavelength. Thus, the second optical means further comprises a lens 54, a filter 55, a collimating lens 56, a dispersive element 57, and a lens 58. Fiber optic bundle 44 does not transmit light via bundle 46 to a photodetector, but rather to lens 54 which focuses the light through a pinhole in filter 55 that restricts the angular spread of the light. The light passing through the pinhole is collimated by lens 56 onto dispersive element 57, which may be a prism or a diffraction grating as shown in FIG. 1.

Grating 57 separates the incident white light into its component wavelengths by a unique angle. For example, the red light rays follow a path defined within dashed lines R and the violet rays follow a path defined within dashed lines V. Lens 58 focuses the separated light onto a linear array 60 of discrete photodetectors, similar to photodetector 48, so that the light in the red path is focused at point 60(r) on one of the photodetectors and the light in the violet path is focused at point 60(v) on another photodetector at the other end of array 60. The light at all intermediate wavelengths is focused at different points along array 60 between points 60(r) and 60(v). Each photodetector measures only a narrow band of wavelengths. The width of each band depends upon the diameter of the pinhole and the width of the corresponding photodetector. In this polychromatic embodiment, the sensing means comprises the array 60 of photodetectors and provides a dark signal and a bright signal for each component wavelength of light measured by a photodetector in array 60. This embodiment is described in more detail in U.S. Pat. No. 4,076,421, the disclosure of which is incorporated herein by reference.

In a first embodiment of optical gate means 30, liquid crystal 32 is a field-effect liquid crystal and backing plate 34 has a reflective surface facing the liquid crystal. Referring in more detail to FIGS. 3 and 4, a field-effect liquid crystal 72 comprises a liquid crystal envelope 73 between transparent electrodes 74 and front and back filters 75 and 76. Front and back filters 75 and 76 are polarized in directions orthogonal to each other. Electrodes 74 are connected to a voltage source 77 via a switch 78 which is opened and closed by a signal provided by signal processor 50 along wire 36. When no field is applied by voltage source 77 as shown in FIG. 3, liquid crystal 72 is transparent so that the reflective surface of backing plate 34 reflects the transmitted portion of the source radiation, rays A, B and C, in the bright state. However, when a field is applied by voltage source 77 as shown in FIG. 4, liquid crystal 72 absorbs the transmitted portion of the source radiation in the dark state.

In a second embodiment of optical gate means 30, liquid crystal 32 is a dynamic-scattering liquid crystal and backing plate 34 has an absorptive surface facing the liquid crystal. Referring in more detail FIGS. 5 and 6, a dynamic-scattering liquid crystal 82 comprises a liquid crystal envelope 83 between transparent electrodes 84 and front and back glass plates 85 and 86. Electrodes 84 are connected to a voltage source 87 via a switch 88 which is opened and closed by a signal provided by signal processor 50 along wire 36. When a field is applied by voltage source 87 as shown in FIG. 5, liquid crystal 82 becomes opaque and frosty so that it reflects the transmitted portion of source 12, rays A(t), B(t) and C(t), in the bright state. However, when the field is removed as shown in FIG. 6, liquid crystal 82 becomes transparent so that the surface of backing plate 34 absorbs the transmitted portion of source radiation in the dark state.

In operation, the monochromatic embodiment is used to provide the dark and bright signals, V(d) and V(b), respectively, as described above so that the reflective opacity of sheet material 2 can be computed. However, the monochromatic embodiment of apparatus 10 is first used to provide a reference signal V(r) necessary for such computation. This is accomplished by using source 12 to directly illuminate (i.e. in the absence of the sheet material 2) optical gating means 30 when switched to the bright state. A portion of source 12 is reflected by optical gating means 30 and the second optical means collects the portion reflected by optical gating means 30 to provide a reference reflectance. The sensing means, photodetector 38, provides the reference signal V(r) which has a magnitude corresponding to the intensity of the reference reflectance. As a result, a standardized reflective opacity R(o) of sheet material 2 can be computed from the bright and dark signals V(b) and V(d) and the reference signal V(r) according to the following equation:

$$R\infty = a - (a^2 - 1)^{\frac{1}{2}} \quad (1)$$

$$a = 0.5 \{V(b) + [V(d) - V(b) + V(r)]/[V(d)*V(r)]\} \quad (2)$$

and V(r) is the reflectance of the optical gating means 30 when switched to the bright state.

The polychromatic embodiment is used in a similar fashion to provide the same signals but for each component wavelength as described above so that the reflectance of the sheet material 2 can be computed for each component wavelength using the above equation. From the resulting plurality of reflectance measurements the color of the sheet material 2 can be computed by known formulae.

Having described the invention by reference to preferred embodiments thereof, it will be apparent that other modifications and variations are possible without departing from the spirit and scope of the invention defined in the appended claims.

What is claimed is:

1. Apparatus for measuring dark and bright reflectances of translucent sheet material, comprising:

first optical means for illuminating one side of the sheet material with a source of optical electromagnetic radiation of substantially uniform intensity, whereby a portion of said reduction is transmitted through the sheet material and another portion of said radiation is reflected by the sheet material;

stationary electrically switchable optical gating means, positioned adjacent the other side of the sheet material in a fixed position relative to said first optical means, for absorbing substantially all of the transmitted portion of said radiation when electrically switched to a dark state and reflecting substantially all of the transmitted portion of said radiation back into the sheet material when electrically switched to a bright state;

second optical means for collecting said reflected portion of said radiation and the portion of said transmitted portion of said radiation reflected by said optical gating means and retransmitted through the sheet material to provide a total reflectance having a dark reflectance intensity when said optical gating means is in said dark state and a bright reflectance intensity when said optical gating means is in said bright state; and sensing means, responsive to said total reflectance provided by said second optical means, for providing a dark signal having a magnitude corresponding to said dark reflectance intensity and a bright signal having a magnitude corresponding to said bright reflectance intensity.

2. Apparatus as in claim 1 wherein said radiation from said source is monochromatic.

3. Apparatus as in claim 1 wherein said first optical means illuminates said optical gating means when switched to said bright state, a portion of said radiation being reflected by said optical gating means, and said second optical means collects said portion reflected by said optical gating means to provide a reference reflectance, and said sensing means provides a reference signal having a magnitude corresponding to the intensity of said reference reflectance.

4. Apparatus as in claim 3 wherein said radiation from said source is monochromatic.

5. Apparatus as in claim 1 wherein said radiation from said source is white light and wherein said second optical means separates said total reflectance into its component wavelength bands, there being a dark reflectance intensity and a bright reflectance intensity for each wavelength band, and said sensing means provides a dark signal and a bright signal for each wavelength band.

6. Apparatus as in claim 5 wherein said first optical means directly illuminates said optical gating means when switched to said bright state, a portion of said radiation being reflected by said optical gating means, and said second optical means collects said portion reflected by said optical gating means to provide a reference reflectance for each wavelength band, and said sensing means provides a reference signal for each wavelength band, each of the reference signals having a magnitude corresponding to the intensity of said reference reflectance for its associated wavelength band.

7. Apparatus as in claim 1, wherein said optical gating means comprises a liquid crystal and a backing plate, said liquid crystal being positioned between the sheet material and said backing plate and having an input for connecting and disconnecting a voltage source to switch said liquid crystal between said dark and bright states.

8. Apparatus as in claim 7 wherein said liquid crystal is a field-effect liquid crystal and said backing plate has a reflective surface facing said liquid crystal so that said liquid crystal absorbs said transmitted portion of said radiation in said dark state when the voltage source is connected to the input thereof and said backing plate reflects said transmitted portion of said radiation in said bright state when the voltage source is disconnected from the input thereof making said liquid crystal transparent.

9. Apparatus as in claim 7 wherein said liquid crystal is a dynamic-scattering liquid crystal and said backing plate has an absorptive surface facing said liquid crystal so that said liquid crystal reflects said transmitted portion of said radiation in said bright state when the voltage source is connected to the input thereof and backing plate absorbs said transmitted portion of said radiation in said dark state when the voltage source is disconnected from the input thererof making said liquid crystal transparent.

10. A method for measuring dark and bright reflectances of translucent sheet material, comprising the steps of:

illuminating one side of the sheet material with a source of optical electromagnetic radiation of substantially uniform intensity, a portion of the radiation being transmitted through the sheet material and another portion of the radiation being reflected by the sheet material;

positioning a stationary electrically switchable optical gate adjacent the other side of the sheet material in a fixed position relative to the source to absorb substantially all of the transmitted portion of the radiation when the optical gate is electrically switched to a dark state and reflect substantially all of the transmitted portion of the radiation back into the sheet material when the optical gate is electrically switched to a bright state;

collecting the reflected portion of the radiation and the portion of the transmitted portion of the radiation reflected by the optical gate and retransmitted through the sheet material to provide a total reflectance having a dark reflectance intensity when the optical gate is in the dark state and a bright reflectance intensity when the optical gate is in the bright state; and providing a dark signal having a magnitude corresponding to the dark reflectance intensity and a bright signal having a magnitude corresponding to the bright reflectance intensity.

11. A method as in claim 10 wherein said radiation from said source is monochromatic.

12. A method as in claim 10 further comprising the steps of directly illuminating the optical gate when switched to the bright state, a portion of the radiation being reflected by the optical gate, collecting the portion reflected by the optical gate to provide a reference reflectance, and providing a reference signal having a magnitude corresponding to the intensity of said reference reflectance so that the opacity of the sheet material can be computed from the reference signal and the bright and dark signals.

13. A method as in claim 12 wherein said radiation from said source is monochromatic.

14. A method as in claim 10 wherein said radiation from said source is white light and further comprising the steps of separating the total reflectance into its component wavelength bands, there being a dark reflectance intensity and a bright reflectance intensity for each wavelength band, and providing a dark signal and a bright signal for each component wavelength band.

15. A method as in claim 14 further comprising the steps of directly illuminating the optical gate when switched to the bright state, a portion of the radiation being reflected by the optical gate, collecting the portion reflected by the optical gate to provide a reference reflectance for each component wavelength band, and providing for each component wavelength band a reference signal having a magnitude corresponding to the intensity of the reference reflectance associated with the component wavelength band so that the color of the sheet material can be computed from the reference signals, bright signals, and dark signals.

16. A method as in claim 10 wherein the optical gate comprises a liquid crystal and a backing plate, and further comprising the steps of positioning the liquid crystal between the sheet material and the backing plate and connecting and disconnecting the input of the liquid crystal to a voltage source to switch the liquid crystal between the dark and bright states.

17. A method as in claim 16 wherein the liquid crystal is a field-effect liquid crystal and the backing plate has a reflective surface facing the liquid crystal, and further comprising the steps of connecting the input of the liquid crystal to the voltage source so that the liquid crystal absorbs the transmitted portion of the radiation in the dark state and disconnecting the input of the liquid crystal from the voltage source so that the liquid becomes transparent and the backing plate reflects the transmitted portion of the source in the bright state.

18. A method as in claim 16 wherein the liquid crystal is a dynamic-scattering liquid crystal and the backing plate has an absorptive surface facing the liquid crystal, and further comprising the steps of connecting the input of the liquid crystal to the voltage source so that the liquid crystal reflects the transmitted portion of the radiation in the bright state and disconnecting the input of the liquid crystal from the voltage source so that the liquid crystal becomes transparent and the backing plate absorbs the transmitted portion of the radiation in the dark state.

* * * * *